United States Patent
Lessing et al.

(10) Patent No.: US 9,272,079 B2
(45) Date of Patent: Mar. 1, 2016

(54) STIMULATION OF CARTILAGE FORMATION USING REDUCED PRESSURE TREATMENT

(71) Applicant: KCI Licensing, Inc., San Antonio, TX (US)

(72) Inventors: Marcus Christian Lessing, San Antonio, TX (US); Braden K. Leung, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 367 days.

(21) Appl. No.: 13/651,148

(22) Filed: Oct. 12, 2012

(65) Prior Publication Data

US 2013/0096492 A1    Apr. 18, 2013

Related U.S. Application Data

(60) Provisional application No. 61/546,622, filed on Oct. 13, 2011.

(51) Int. Cl.
*A61M 1/00* (2006.01)
*A61M 5/14* (2006.01)
*A61L 27/38* (2006.01)

(52) U.S. Cl.
CPC .......... *A61M 1/0023* (2013.01); *A61L 27/3817* (2013.01); *A61M 1/008* (2013.01);
(Continued)

(58) Field of Classification Search
CPC ............ A61M 1/0039; A61M 1/0023; A61M 1/0058; A61M 1/008; A61M 5/14
USPC ....................................... 604/28, 19, 35, 500
See application file for complete search history.

(56) References Cited

U.S. PATENT DOCUMENTS 1,355,846 A    10/1920   Rannells
2,547,758 A    4/1951    Keeling
(Continued)

FOREIGN PATENT DOCUMENTS

AU    550575 A1    8/1982
AU    745271       4/1999
(Continued)

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (certified translation).
(Continued)

*Primary Examiner* — Edelmira Bosques
*Assistant Examiner* — Leah Swanson

(57) ABSTRACT

System and methods for stimulating cartilage formation at a first tissue site through a second tissue site is presented. The system includes a fluid source for supplying a therapeutic solution, a reduced pressure source for supplying reduced pressure, a fluid delivery manifold for deploying adjacent the first tissue site, and a vacuum manifold for deploying within the second tissue site. The fluid delivery manifold extends between a proximal end fluidly coupled to the fluid supply and a distal end having at least one aperture for delivering the therapeutic solution to the defect adjacent the articulating surface of the first tissue site. The vacuum manifold extends between a proximal end fluidly coupled to the reduced pressure source and a distal end having at least one aperture for delivering the reduced pressure to the first tissue site adjacent the opposing surface of the first tissue site.

7 Claims, 9 Drawing Sheets

(52) U.S. Cl.
CPC .............. *A61M 1/0058* (2013.01); *A61M 5/14* (2013.01); *A61L 2300/434* (2013.01); *A61L 2430/06* (2013.01); *A61L 2430/14* (2013.01); *A61L 2430/24* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Guiles, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,842,578 A * | 6/1989 | Johnson et al. ................. 604/22 |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,616,121 A | 4/1997 | McKay |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0030281 A1 | 2/2004 | Goble |
| 2007/0128155 A1 * | 6/2007 | Seyedin et al. ............ 424/78.37 |
| 2009/0326423 A1 | 12/2009 | Girouard |
| 2010/0168688 A1 | 7/2010 | Santora |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastman, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
International Search Report and Written Opinion for PCT International Application PCT/US2012/060106 mailed Jan. 25, 2013.

\* cited by examiner

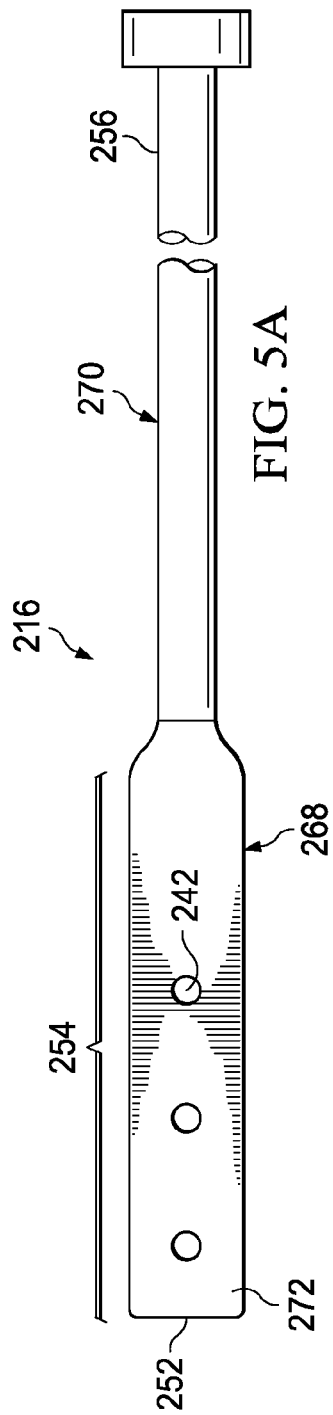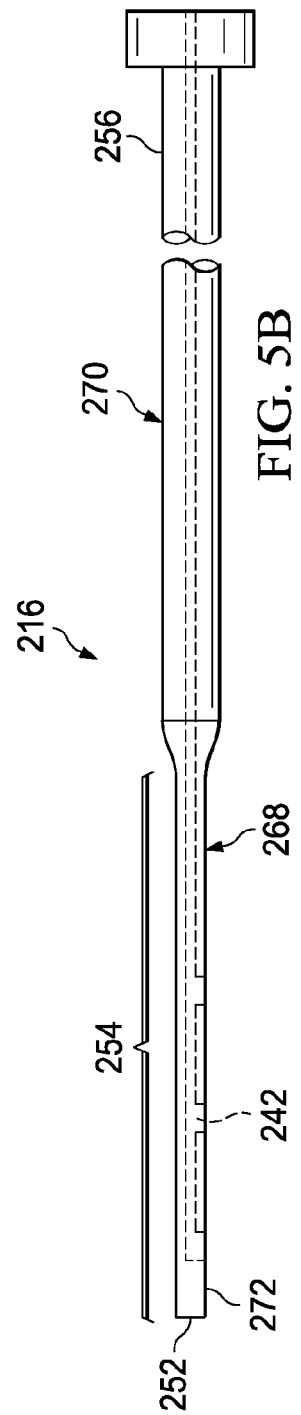

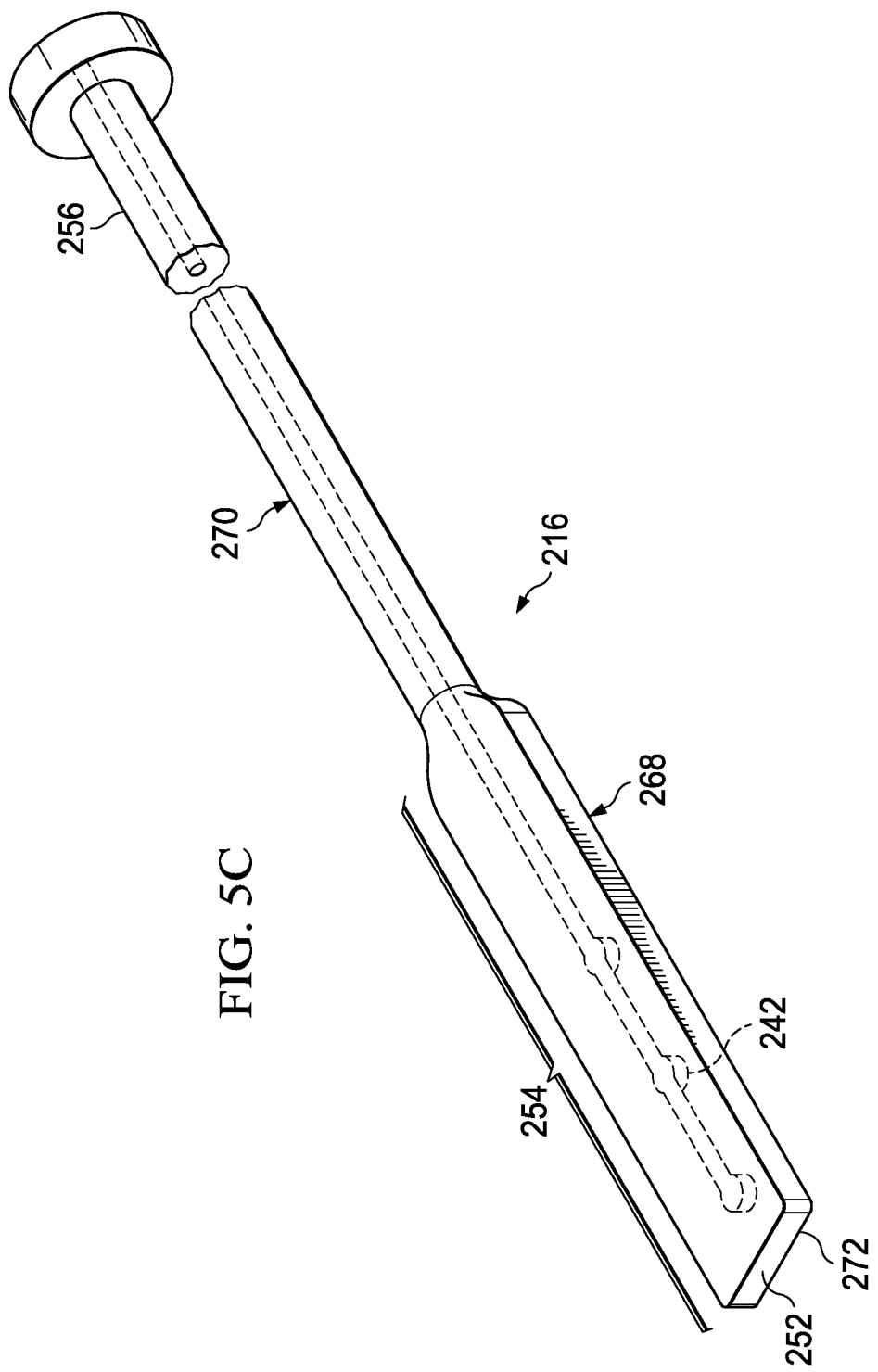

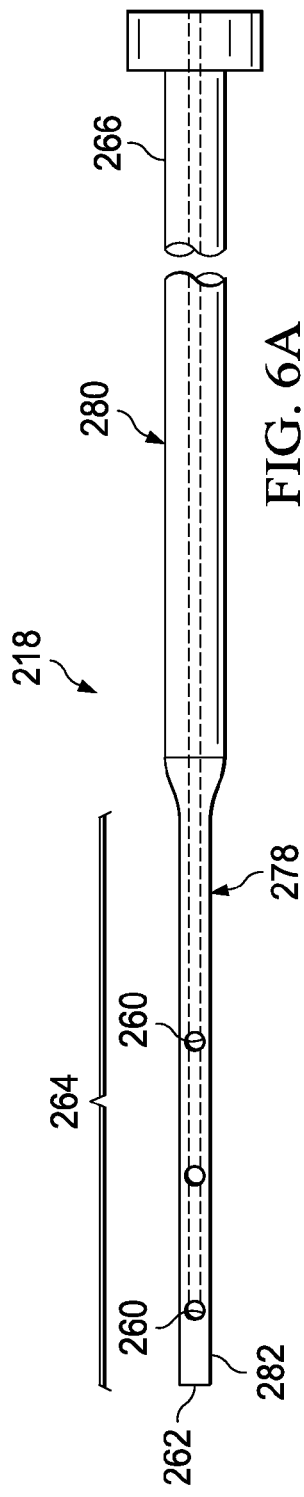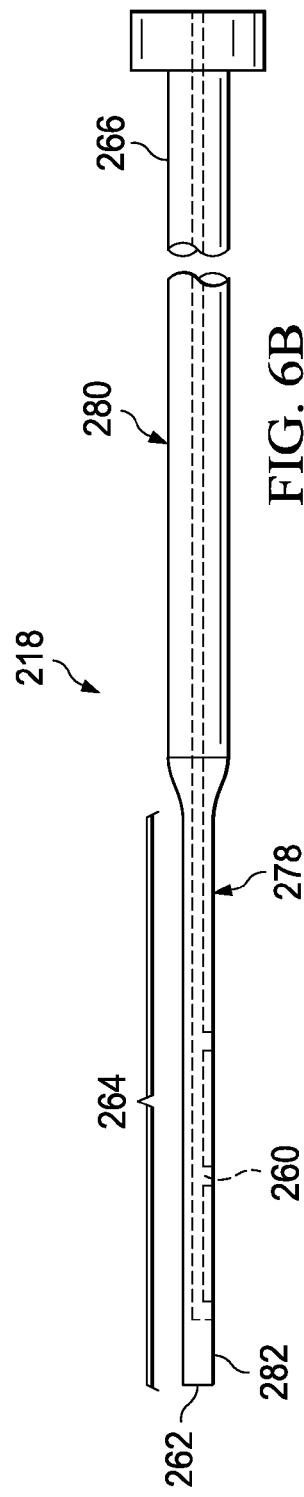

STIMULATION OF CARTILAGE FORMATION USING REDUCED PRESSURE TREATMENT

The present invention claims the benefit, under 35 USC §119(e), of the filing of U.S. Provisional Patent Application Ser. No. 61/546,622, entitled "Stimulation of Cartilage Formation using Reduced Pressure Treatment," filed Oct. 13, 2011, by Lessing et al., which is incorporated herein by reference for all purposes.

BACKGROUND OF THE INVENTION

1. Field of the Invention

The present invention relates generally to tissue treatment systems and in particular to the stimulation of cartilage formation using reduced pressure treatment 2. Description of Related Art Clinical studies and practice have shown that providing a reduced pressure in proximity to a tissue site augments and accelerates the growth of new tissue at the tissue site The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. Unless otherwise indicated, as used herein, "or" does not require mutual exclusivity. The porous pad, often an open-cell foam, contains cells or pores that are capable of distributing reduced pressure to the tissue and channeling fluids that are drawn from the tissue. The porous pad often is incorporated into a dressing having other components that facilitate treatment. While reduced pressure therapy has been used to treat soft tissue injuries, such therapy has not been used extensively to promote, for example, cartilage regeneration.

Damage to cartilage through age, injury, wear, and metabolic disorders, such as osteoarthritis, affect millions of people throughout the world. Indeed, it is currently believed that 85% of all Americans will develop degenerative joint disease as a result of normal activities that damage cartilage. The gradual degeneration and destruction of articular cartilage, one of three different types of cartilage, may be due to trauma, structural deformation of the joints and being overweight. Articular cartilage is a highly organized avascular tissue composed of chondrocytes formed in an extracellular matrix. Articular cartilage is generally thin with an extremely low or insignificant blood flow and, as such, has a very limited ability to repair or heal itself Partial-thickness chondral defects, for example, cannot spontaneously heal. This tissue is extremely important to the normal, healthy function and articulation of joints. Articular cartilage enables joint motion surfaces to articulate smoothly with a very low coefficient of friction. It also acts as a cushion to absorb compressive, tensile, and shearing forces and, thus, helps protect the ends of bone and surrounding tissue. The clinical manifestations of cartilage damage or wear are often painful and debilitating, including swelling of the joint, crepitation, and decrease in functional mobility. As the condition worsens, pain may even limit minimum physical efforts and persist at rest making it difficult to sleep. If the condition persists without correction and/or therapy, the joint can be totally destroyed, leading the patient to major replacement surgery with a total prosthesis, or to disability. The complications of cartilage injury are multifold. For example, injured cartilage tends to cause additional damage to articulations and the articular surfaces. Damage to articular surfaces is linked to bone spur development, which further limits joint movement.

The other two types of cartilage are fibrocartilage and elastic cartilage. Fibrocartilage offers strength with flexibility while providing shock absorption against impact and tensile forces. Fibrocartilage may be found in several areas of the body including, the annulus fibrosus of the intervertebral discs and the meniscus located in the knee joint. Elastic cartilage may provide flexibility and structural support to portions of the body. Elastic cartilage may also be found in several areas of the body including, the outer ear, the larynx, and the epiglottis. Fibrocartilage and elastic cartilage may also be damaged from injuries or degeneration. The damaged cartilage may be painful and debilitating and may further result in cosmetic defects. Consequently, damaged cartilage can have sweeping effects on the body that may ultimately lead to a reduced quality of life.

Typically, the body cannot completely repair the cartilage. Cartilage is primarily composed of collagen fibers, proteoglycans and elastin fibers that form an extracellular matrix. The matrix is formed by specialized cells called chondrocytes. Chondrocytes are one of the few cell types that can survive with a minimal blood supply. However, when cartilage is damaged, the lack of an adequate blood supply to the chondrocytes results in an inability to regenerate new chondrocytes, a process that requires an increased amount of nutrients and access through the blood stream to other cells and proteins. Full thickness articular cartilage damage that exposes the subchondral bone or osteochondral lesions may generate a normal inflammatory response that repairs the cartilage, but the new fibrocartilage formation is functionally inferior.

Current techniques to inhibit or delay degeneration of joint cartilage include use of anti-inflammatory agents, chondrogenic stimulating factors, antirheumatics, systemics, viscoprotection and injection of depot steroids. Other methods to inhibit or delay degeneration of joint cartilage include implantation of chondrocytes or synthetic matrices. One method of treatment for cartilage damage is surgical intervention, with reattachment and reconstruction of the damaged tissue. None of the above methods are totally satisfactory, and those methods rarely restore full functionality or return the tissue to its native normal state. In addition, none of those methods are proven to regenerate cartilage in situ and in vivo.

SUMMARY

According to an illustrative embodiment, a system for stimulating formation of cartilage at a defect in a first tissue site having an articulating surface within a joint and an opposing surface adjacent a second tissue site is described. The system includes a fluid source for supplying a therapeutic solution, a reduced pressure source for supplying reduced pressure, a fluid delivery manifold for deploying adjacent the first tissue site, and a vacuum manifold for deploying within the second tissue site The fluid delivery manifold has a tubular body extending between a proximal end fluidly coupled to the fluid supply and a distal end having at least one aperture for delivering the therapeutic solution to the defect adjacent the articulating surface of the first tissue site, and the tubular body is dimensioned to fit within the joint adjacent the defect. The vacuum manifold has a tubular body extending between a proximal end fluidly coupled to the reduced pressure source and a distal end having at least one aperture for delivering the reduced pressure to the first tissue site adjacent the opposing surface of the first tissue site The tubular body of the vacuum manifold is dimensioned to be inserted into the second tissue site adjacent the opposing surface of the first tissue site to deliver reduced pressure through the second tissue site to the first tissue site to draw the therapeutic solution from the fluid delivery manifold through the first tissue site and the defect.

According to another illustrative embodiment, a system for stimulating formation of new cartilage at a defect in cartilage having a first face and a second face opposing the first face adjacent skin tissue is described. The system includes a fluid source for supplying a therapeutic solution, a reduced pressure source for supplying reduced pressure, a fluid delivery manifold for deploying adjacent the first face of the cartilage, and a vacuum manifold for deploying within the second face of the cartilage. The fluid delivery manifold has a tubular body extending between a proximal end fluidly coupled to the fluid supply and a distal end having at least one aperture for delivering the therapeutic solution to the defect adjacent the first face of the cartilage. The vacuum manifold has a tubular body extending between a proximal end fluidly coupled to the reduced pressure source and a distal end having at least one aperture for delivering the reduced pressure through the skin tissue to the defect adjacent the second face of the cartilage to draw the therapeutic solution from the fluid delivery manifold adjacent the first face through the cartilage and the defect.

According to another illustrative embodiment, a method for stimulating formation of cartilage at a defect in a first tissue site having an articulating surface within a joint and an opposing surface adjacent a second tissue site is described. The method includes positioning the distal end of a fluid delivery manifold having at least one aperture within the joint adjacent the articulating surface of the first tissue site, and connecting the proximal end of the fluid delivery manifold to a fluid source containing a therapeutic solution. The method further comprises positioning the distal end of a vacuum manifold having at least one aperture within the second tissue site adjacent the opposing surface of the first tissue site, and connecting the proximal end of the vacuum manifold to a reduced pressure source for delivering reduced pressure to the first tissue site The method also comprises delivering the therapeutic solution to the articulating surface of the first tissue site, and delivering the reduced pressure through the second tissue site to the first tissue site to draw the therapeutic solution from the fluid delivery manifold through the first tissue site and the defect.

According to another illustrative embodiment, a method for stimulating formation of new cartilage at a defect in cartilage having a first face and a second face opposing the first face adjacent skin tissue covering the cartilage is described. The method includes positioning the distal end of a fluid delivery manifold having at least one aperture within the joint adjacent the first face of the cartilage, and connecting the proximal end of the fluid delivery manifold to a fluid source containing a therapeutic solution. The method further comprises positioning the distal end of a vacuum manifold having at least one aperture adjacent the second face of the cartilage, and connecting the proximal end of the vacuum manifold to a reduced pressure source for delivering reduced pressure to the first face of the cartilage. The method also comprises delivering the therapeutic solution to the first face of the cartilage and the defect, and delivering the reduced pressure through the skin tissue to the defect adjacent the second face of the cartilage to draw the therapeutic solution from the fluid delivery manifold adjacent the first face through the cartilage and the defect.

According to yet another illustrative embodiment, a method for stimulating cartilage formation at a defect in a first bone of two bones forming a joint includes positioning a first manifold between the two bones and a second manifold within the first bone. The first manifold is deployed adjacent a first face of the defect and the second manifold is deployed adjacent a second, opposing face of the defect.

Other objects, features, and advantages of the illustrative embodiments will become apparent with reference to the drawings and detailed description that follow.

BRIEF DESCRIPTION OF THE DRAWINGS

FIG. 5A is a schematic top view of an illustrative embodiment of a fluid delivery manifold for use in the reduced-pressure treatment system of FIG. 1;

FIG. 5B is a schematic side view of the fluid delivery manifold of FIG. 5A;

FIG. 5C is a schematic perspective view of the fluid delivery manifold of FIG. 5A;

FIG. 6A is a schematic top view of an illustrative embodiment of a fluid delivery manifold for use in the reduced-pressure treatment system of FIG. 1;

FIG. 6B is a schematic side view of the fluid delivery manifold of FIG. 6A;

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "tissue site" as used herein refers to the location of a wound, fracture, or other defect on or within any tissue, including but not limited to, bone tissue, muscle tissue, connective tissue, and cartilage, such as elastic cartilage, articular cartilage, or fibrocartilage. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
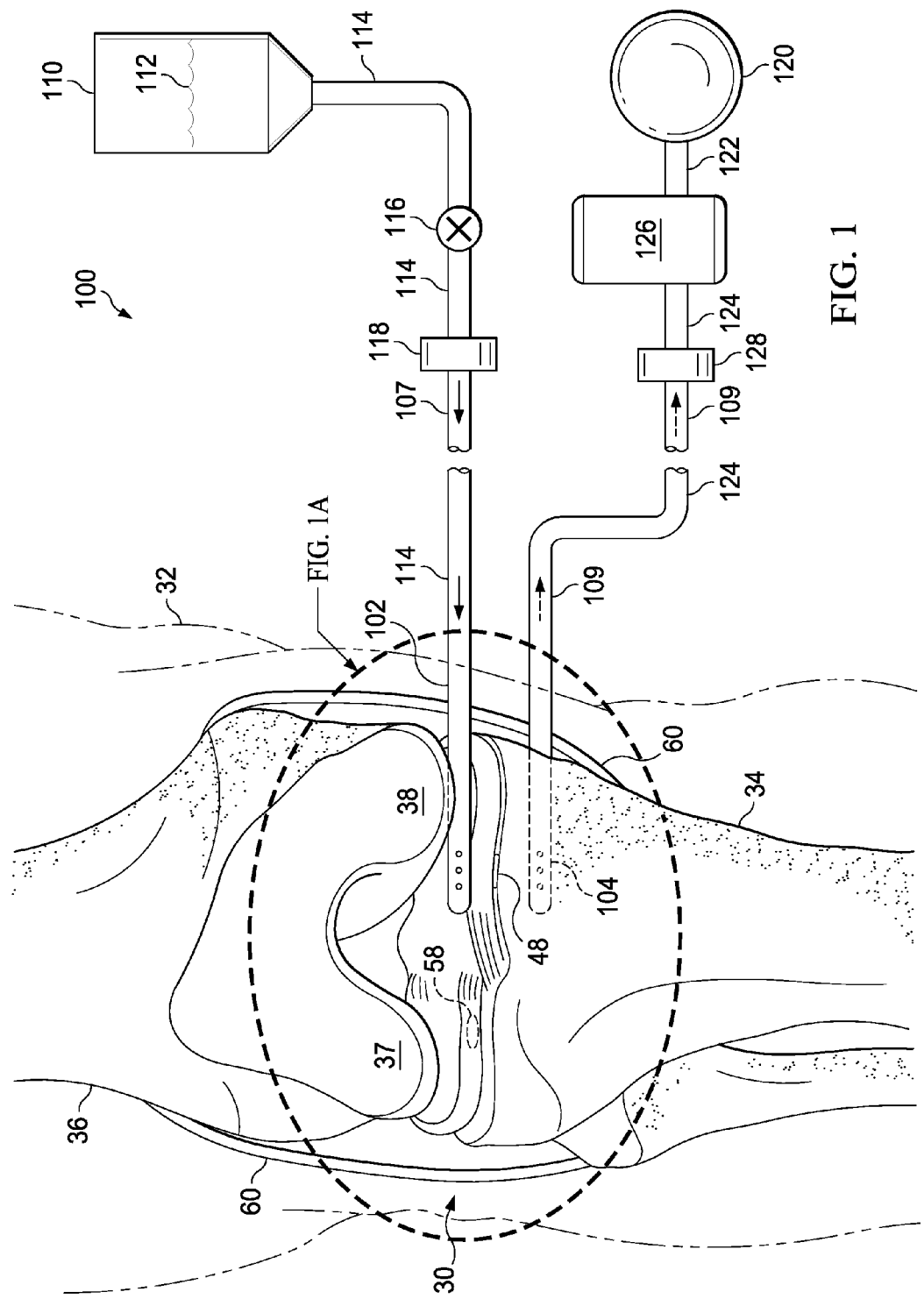
FIG. 1 is a schematic diagram of a reduced-pressure treatment system for repairing cartilage in a right knee joint that includes a fluidic system and a reduced pressure system.
Figure 2:
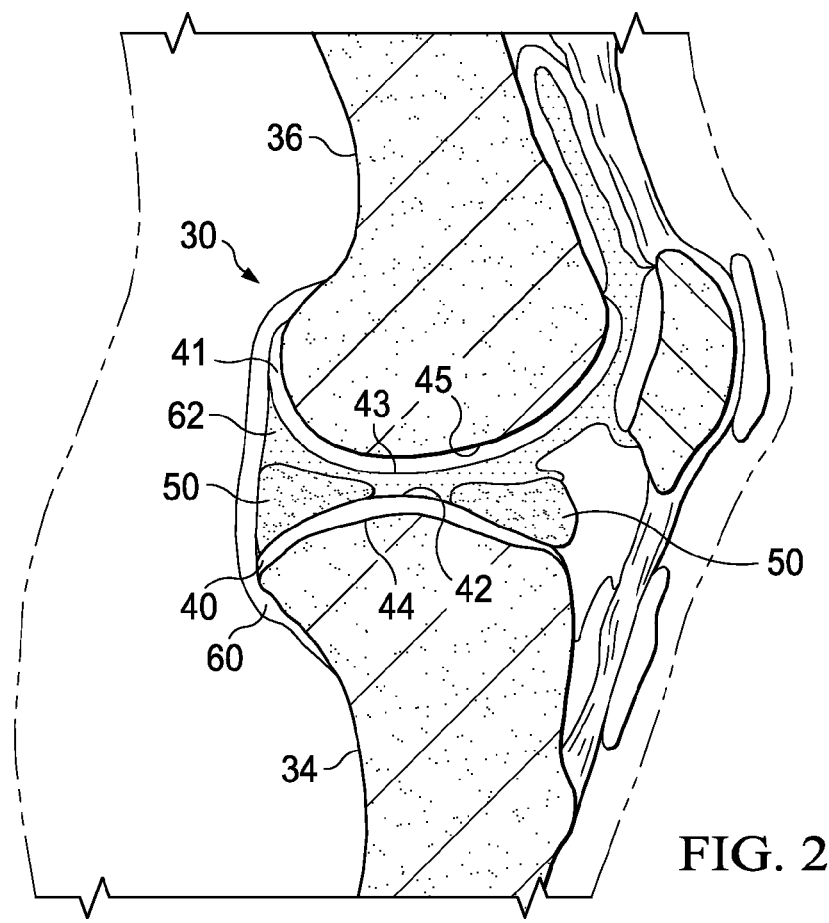
FIG. 2 is a pictorial, cross-sectional view of a right knee joint, such as the right knee joint of FIG. 1 taken along the saggital plane.
Figure 3:
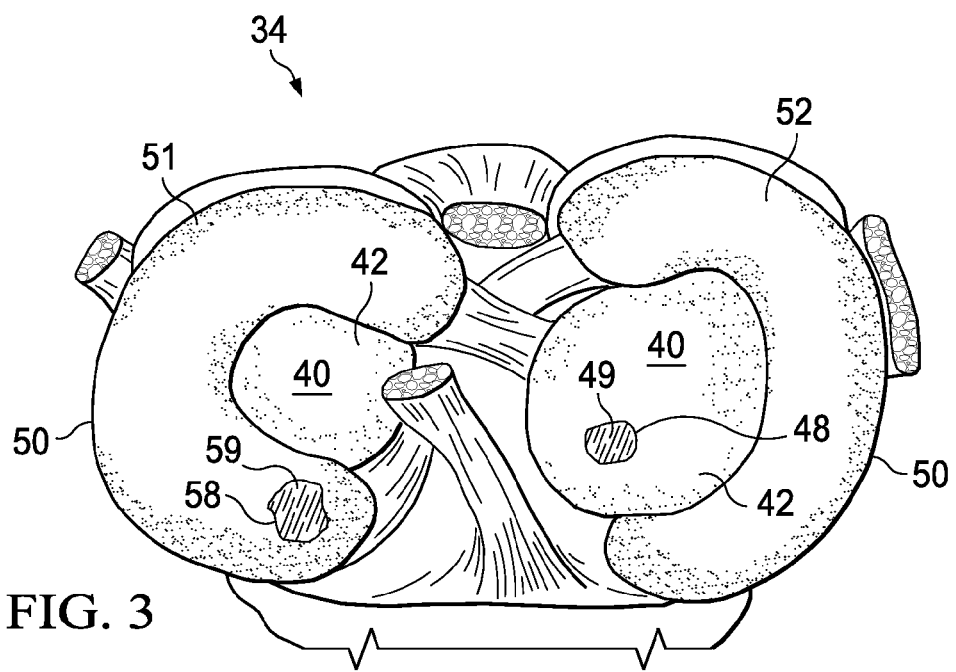
FIG. 3 is a pictorial, top view the tibia, such as the tibia of FIG. 1, showing the fibrocartilage and the articular cartilage attached to the tibia.

As previously mentioned, the body includes three different types of cartilage having distinctly different structures and distinctly different functions. Of the three types of cartilage found in the body, both the articular cartilage and the fibro-cartilage are found in the knee. Referring more specifically to FIGS. 1-3, a knee joint 30 of a human leg 32 (the right leg) comprising a tibia 34 and a femur 36, having lateral and medial condyles 37, 38, are shown. The knee joint 30 further comprises a lower articular cartilage 40 that covers the head of the tibia 34 and an upper articular cartilage 41 that covers the heads of the condyles 37, 38. The articular cartilages 40, 41 provide articulating surfaces 42 and 43, respectively, to facilitate articulation between the tibia 34 and the condyles 37, 38. Correspondingly, each of the articular cartilages 40, 41 have interfacing surfaces 44 and 45, respectively, that are opposite-facing and generally parallel to the articulating surfaces 42, 43 and interface with the bone tissue of the tibia 34 and the condyles 37, 38, respectively. The knee joint 30 also comprises fibro-cartilage which is also referred to as the meniscus 50 that includes two semilunar pads of fibro-cartilage, the lateral meniscus 51 and the medial meniscus 52, each having articulating surfaces 53 and 54, respectively, to further disperse friction between the tibia 34 and the condyles 37, 38. Correspondingly, the lateral and medial meniscus 51, 52 have interfacing surfaces 55 and 56, respectively, that are generally opposite-facing to the articulating surfaces 53, 54 and interface with the bone tissue of the tibia 34. The articulating surfaces 53, 54 are concave to support the condyles 37, 38 that fit into and articulate within the cups of the meniscus 50. The knee joint 30 further comprises a synovial membrane 60 that surrounds an inter-articular space 62 between the articulating surface 43 of the upper articular cartilage 41 and the articulating surfaces 42, 53, 54 of the lower articular cartilage 40 and the meniscus 50.

Figure 1A:
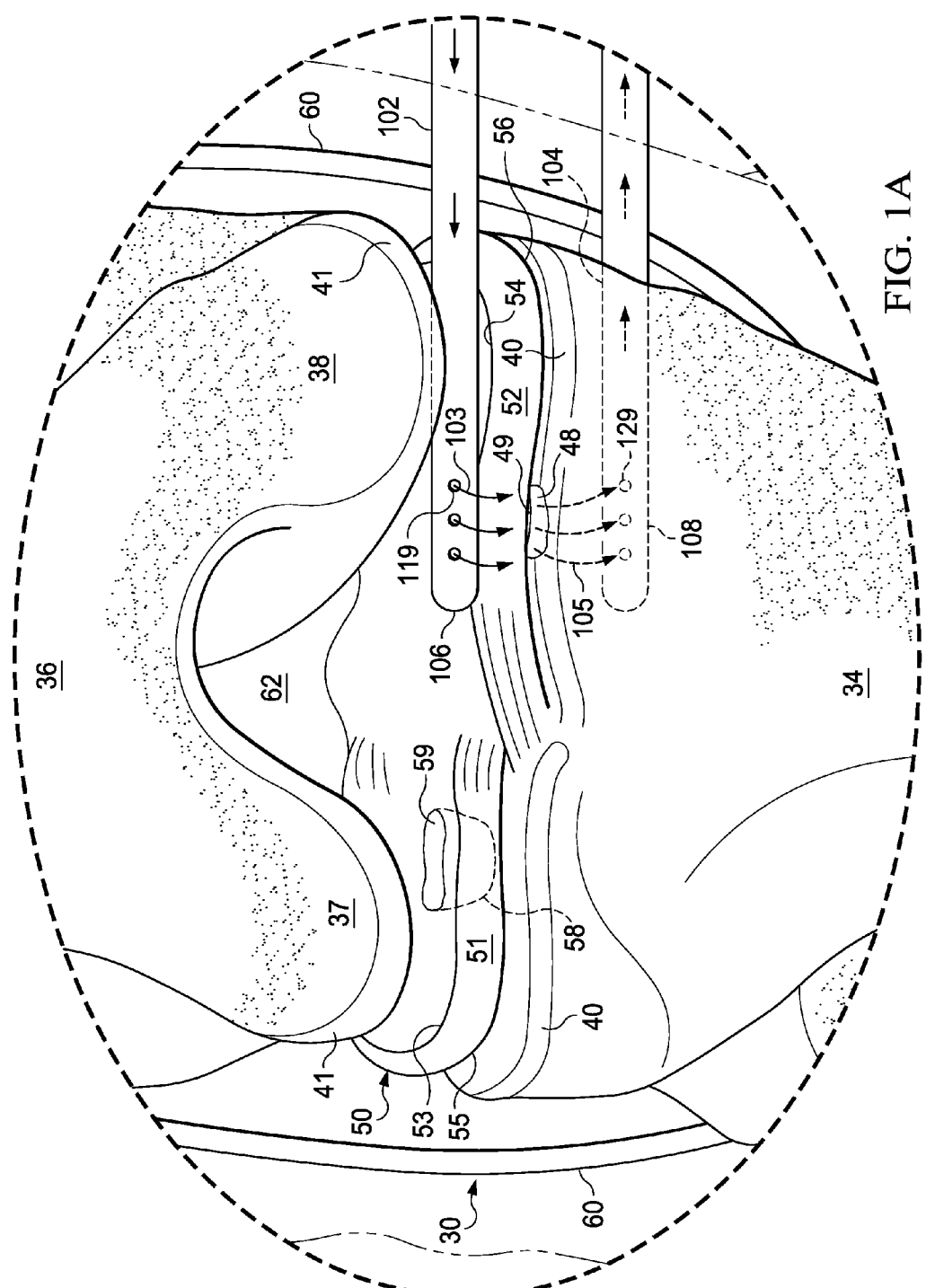
FIG. 1A is a detailed view of the right knee joint of FIG. 1.

Cartilage defects may be caused by trauma, surgery, wear, arthritis, or cancer as described above, or may be congenital. More specifically, in the illustrated embodiment, the lower articular cartilage 40 and the meniscus 50 also may be damaged by such incidents resulting in various types of defects in both types of cartilage, i.e., articular defects 48 in the lower articular cartilage 40 and meniscus defects 58 in the meniscus 50, collectively the cartilage defects, located at a tissue site in the knee joint 30. Referring more specifically to FIGS. 1 and 1A, an illustrative embodiment of a reduced-pressure therapy system 100 for stimulating cartilage formation in the cartilage defects of the tissue site is shown. The system 100 comprises a fluid delivery manifold 102 for being deployed into the synovial membrane 60 adjacent the upper articulating surface 43 of the upper articular cartilage 41 and the articulating surfaces 53, 54 of the meniscus 50 including the articulating surfaces of the cartilage defects, i.e., an articular defect surface 49 of the articular defect 48 and a meniscus defect surface 59 of the meniscus defect 58. The fluid delivery manifold 102 may be used for delivering a therapeutic solution 112 to the defect surfaces 49, 59 of the cartilage defects from within the synovial membrane 60 as indicated by solid arrows 103. The system 100 further comprises a vacuum manifold 104 for deploying into the head of the tibia 34 adjacent the lower interfacing surface 44 of the lower articular cartilage 40 and/or, the interfacing surfaces 55, 56 of the lateral and medial meniscus 51, 52 below or contiguous with lower portions of the articular defect 48 and the meniscus defect 58. The vacuum manifold 104 may be used for delivering reduced pressure to the interfacing surfaces 44, 55, 56 from within the head of the tibia 34 as indicated by the dashed arrows 105.

Providing reduced pressure within the head of the tibia 34 draws the therapeutic solution 112 through the lower articular cartilage 40 and/or the meniscus 50 from the articular and meniscus defect surfaces 49, 59 of the cartilage defects to the lower portions of the articular defect 48 and the meniscus defect 58. Application of the reduced pressure to draw therapeutic solution through the articular cartilage 40 and/or the meniscus 50 and the tissue forming the head of the tibia 34 significantly enhances the flow and dispersion of the therapeutic solution to increase the amount of cartilage formation for repairing the cartilage defects, as compared to application of therapeutic solution to only the articular or meniscus defect surfaces 49, 59. Additionally, the system may provide for multiple treatment sessions after deploying the fluid delivery manifold 102 and the vacuum manifold 104 adjacent the tissue site in contrast to treatment regimens that require repeated injections and positioning of a needle. Clearly, the system 100 may be used in a similar fashion to disperse therapeutic solution to repair cartilage defects in the upper articular cartilage 41 by changing the position of the manifold to be in the femur 36. It should be understood that the system 100 may be used for other joints of the body between articulating surfaces, and in other areas of the body where cartilage growth may be desired. It should also be understood that the system 100 may also be used for the removal of fluids from the tissue site including, for example, the removal of exudates and excess therapeutic solution, and for the delivery of other fluids including, for example, saline and other fluids containing materials such as growth factors for facilitating the growth of cartilage.

The system 100 further comprises a fluid supply 110 that contains a therapeutic solution 112 or other fluid as described above. The fluid supply 110 is connected to the fluid delivery manifold 102 via a conduit 114 which includes a valve 116 for controlling the flow of fluid through the conduit 114. The fluid supply 110 is operable to deliver the therapeutic solution 112 to the fluid delivery manifold 102 by relying on simple gravity feed or by applying a positive pressure (not shown) to the therapeutic solution 112. The therapeutic solution 112 may include a number of agents targeted for treating the cartilage defects. In a specific, non-limiting example, the therapeutic solution 112 may include a cell suspension, soluble molecules, bioactive factors, chondrocytes, bone marrow stromal cells, stem cells, or collagen, either alone or in any desirable combination. The therapeutic solution 112 may include protease inhibitors to counteract increased amounts of proteases that may be found, for example, in fluid surrounding osteoarthritic joints, as proteases may cause degradation of cartilage. Additionally, the therapeutic solution 112 may include hyaluronic acid which has been used to treat pain caused from cartilage defects.

The fluid delivery manifold 102 may be an elongated tube having a distal end 106 that is closed and a proximal end 107 fluidly coupled to the conduit 114 by a connector 118. The fluid delivery manifold 102 may have a cross-section that is generally circular in shape or flattened as necessary to fit within the synovial membrane 60 between the tibia 34 and the condyles 37, 38. In one embodiment, the fluid delivery manifold 102 is a tube having a circular cross-section with a diameter sufficiently sized to fit between the tibia 34 and the condyles 37, 38. For example, the distal end 106 may have diameter between about 1 mm and about 12 mm. In one embodiment of the fluid delivery manifold 102, the elongated tube is formed from a silicone material, but may also be formed from a variety of known medical grade tubing. The fluid delivery manifold 102 further includes one or more apertures 119 or fenestrations located adjacent the distal end 106 for delivering the therapeutic solution 112 to the defect surfaces 49, 59 as described above and shown by the solid arrows 103. The apertures 119 may be positioned on the fluid delivery manifold 102 to direct the flow of the therapeutic solution 112 in a direct stream toward the defect surfaces 49, 59 or in multiple directions as required by the specific therapeutic treatment. Although the apertures 119 are arranged in a single row facing a single direction as shown, it should be appreciated that the apertures 119 may be staggered or aligned around the circumference of the fluid delivery manifold 102 to direct the therapeutic solution 112 in multiple directions. The fluid delivery manifold 102 may also be positioned to direct therapeutic solution 112 in various directions to optimize the therapeutic treatment The apertures 119 may be formed in variety of different shapes such as, for example, circular, oblong, or square. In one embodiment, the apertures 119 are slits. As indicated above, the apertures 119 are positioned along the longitudinal axis of the fluid delivery manifold 102. However, it should be understood that the length of the tube over which the apertures 119 are positioned depends on the on the size of the tissue site being treated. The fluid delivery manifold 102 may be manufactured as one piece or alternatively pieced together.

The fluid supply 110 may be operable to provide a continuous supply of therapeutic solution 112 to the tissue site In another embodiment, the fluid supply 110 may be operable to supply the therapeutic solution 112 to the tissue site according to a treatment schedule determined by a healthcare provider. Regardless of whether the therapeutic solution 112 is applied continuously or dynamically, the therapeutic solution 112 is applied without the need for repositioning of the fluid delivery manifold 102. Thus, the fluid delivery manifold 102 may remain in a fixed position within the synovial membrane 60 during all phases of fluid delivery, even during those time periods when no therapeutic solution 112 is being delivered to the tissue site within the synovial membrane 60.

The system 100 further comprises a reduced pressure source 120 fluidly coupled to the vacuum manifold 104. The reduced pressure source 120 is operable to supply reduced pressure to the vacuum manifold 104 which distributes the reduced pressure within the head of the tibia 34 adjacent the interfacing surface 44 of the lower articular cartilage 40 as described above. The reduced pressure source 120 is fluidly coupled to the vacuum manifold 104 by conduits 122, 124 including a canister 126 having a filter (not shown) fluidly coupled between the two conduits 122, 124. The canister 126 may be a fluid reservoir, or collection member, to filter and hold exudates and other fluids removed from the tissue site via the vacuum manifold 104. The canister 126 may include other devices (not shown) including the following non-limiting examples: a pressure-feedback device, a volume detection system, a blood detection system, an infection detection system, a flow monitoring system, and a temperature monitoring system. Some of these devices may be formed integral with the reduced pressure source 120.

The reduced pressure source 120 may be any device for supplying a reduced pressure, such as a vacuum pump, wall suction, or other source. While the amount and nature of reduced pressure applied to a tissue site will typically vary according to the application, the reduced pressure will typically be between −5 mm Hg and −500 mm Hg and more typically between −100 mm Hg and −300 mm Hg. The particular protocol used in reduced pressure treatment depends upon several factors including, for example, the location of the tissue site, i.e., whether a knee joint or some other joint in the body, the type of reduced pressure dressing, and the pharmacological agents being utilized in the therapeutic solution.

The vacuum manifold 104 may also be an elongated tube having a distal end 108 that is closed and a proximal end 109 fluidly coupled to the conduit 124 by a connector 128. The vacuum manifold 104 may have a cross-section that is generally circular in shape or flattened as necessary to fit within the head of the tibia 34 below the interfacing surface 44 of the lower articular cartilage 40. In one embodiment, the vacuum manifold 104 is a tube having a circular cross-section with a diameter sufficiently sized to fit between the tibia 34 and the condyles 37, 38. For example, the distal end 108 may have a diameter between about 1 mm and about 12 mm. In one embodiment of the vacuum manifold 104, the elongated tube is formed from a silicone material, but may also be formed from a variety of known medical grade tubing. The vacuum manifold 104 further includes one or more apertures 129 or fenestrations located adjacent the distal end 108 for delivering reduced pressure to the interfacing surfaces 44, 55, 56 from within the head of the tibia 34 as indicated by the dashed arrows 105. Providing reduced pressure within the head of the tibia 34 draws the therapeutic solution through the lower articular cartilage 40 and/or the meniscus 50 from the articular and meniscus defect surfaces 49, 59 of the cartilage defects to the lower portions of the articular defect 48 and the meniscus defect 58. The apertures 129 may be positioned on the vacuum manifold 104 to direct the reduced pressure to a single location on the interfacing surface 44 of the lower articular cartilage 40 toward the lower portions of the defect surfaces 49, 59 or direct the reduced pressure hi multiple directions as required by the specific therapeutic treatment. Although the apertures 129 are arranged in a single row facing a single direction as shown, it should be appreciated that the apertures 129 may be staggered or aligned around the circumference of the vacuum manifold 104 to direct the reduced pressure in multiple directions. The vacuum manifold 104 may also be positioned to draw the therapeutic solution 112 in various directions to optimize the therapeutic treatment The apertures 129 may be formed in variety of different shapes such as, for example, circular, oblong, or square. In one embodiment, the apertures 129 are slits. As indicated above, the apertures 129 are positioned along the longitudinal axis of the vacuum manifold 104. However, it should be understood that the length of the tube over which the apertures 129 are positioned depends on the on the size of the tissue site being treated. The vacuum manifold 104 may be manufactured as one piece or alternatively pieced together.

Figure 4:
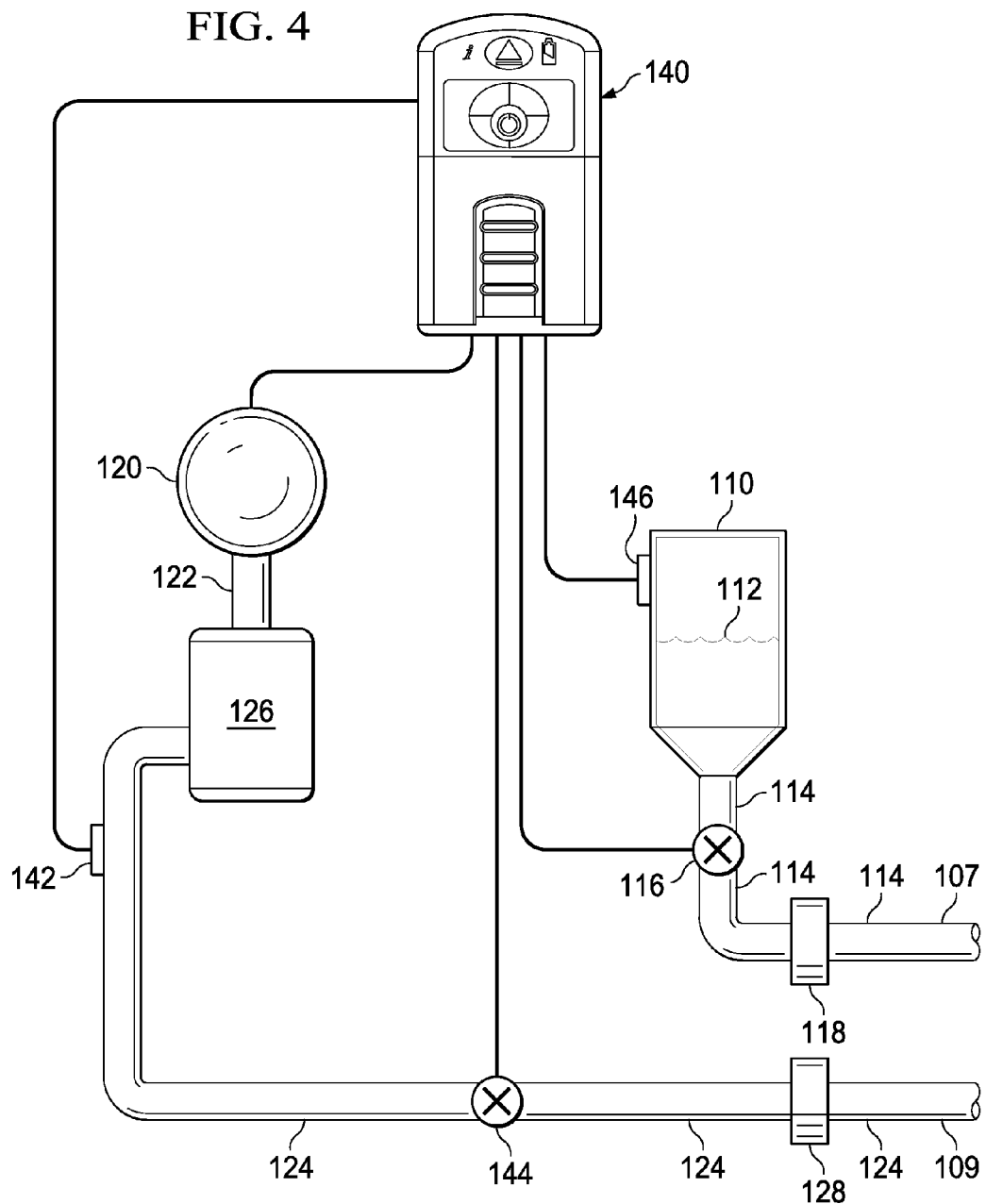
FIG. 4 is a schematic view of a control system for the reduced-pressure treatment system.

Referring now to FIGS. 1 and 4, the system 100 includes a control unit 140 that is electrically connected to the fluid supply 110 and the reduced pressure source 120. The control unit 140 may include sensors, processing units, alarm indicators, memory, databases, software, display units, and user interfaces that further facilitate the treatment of the tissue site. In one example, a sensor or switch 142 electrically connected to the control unit 140 may be disposed at or near the reduced pressure source 120 to determine a source pressure generated by the reduced pressure source 120. The sensor 142 provides feedback to the control unit 140 which regulates the reduced pressure therapy being applied by the reduced pressure source 120 to the tissue site. The control unit 140 may be operatively connected to a valve 144 positioned within the conduit 124 to further control the amount of reduced pressure delivered to the head of the tibia 34 to create the flow of fluids as described above. The control unit 140 may be operatively connected to the valve 116 to control the delivery of the therapeutic solution 112 to the synovial membrane 60. The control unit 140 may also be in fluid communication with the fluid supply 110 via a connector 146 to apply a positive pressure to the therapeutic solution 112 to assist in the delivery of the therapeutic solution 112 to the synovial membrane 60. The control unit 140 may be programmed such that the system 100 simultaneously delivers the therapeutic solution 112 and the reduced pressure. It should be appreciated that the control unit may be programmed to deliver the therapeutic solution 112 and the reduced pressure in any combination according to the therapeutic treatment protocol being administered.

In operation, the system 100 may be used for stimulating cartilage formation of any one of the three types of cartilage described above. In a specific, non-limiting illustration, the system may be used to stimulate cartilage between articulating joints such as the knee joint 30. Using the knee joint 30 for illustration purposes, a method for stimulating cartilage formation using the system 100 will be described. An incision is made next to the knee joint 30 such as in the synovial membrane 60 surrounding the knee joint 30. The fluid delivery manifold 102 is inserted into the incision such that the apertures 119 are positioned adjacent or proximate to the defect surfaces 49, 59. The fluid delivery manifold 102 is positioned in the intra-articular space 62 between the two articulating surfaces, the femur 36 and the tibia 34. The fluid delivery manifold 102 is connected to the fluid supply 110. In this illustration, the defects 48, 58 are located adjacent the tibia 34. Thus, a hole is drilled in the tibia 34, or the subchondral bone, underneath the defects 48, 58. The vacuum manifold 104 is then positioned within the hole so that the vacuum manifold 104 is positioned beneath the defects 48, 58. To describe the positional relationship of the defects 48, 58 relative to the vacuum manifold 104 and fluid delivery manifold 102 in another way, the defects 48, 58 are located between the vacuum manifold 104 and the fluid delivery manifold 102 such that the vacuum manifold 104 and the fluid delivery manifold 102 are generally on opposing faces of the defects 48, 58. The subchondral bone is the bone below the defects 48, 58 or is the bone that supports the cartilage being treated. In this instance, the tibia 34 is the subchondral bone. However, it should be understood that the subchondral bone depends on the location of the defect. For example, if there was a defect in the articular cartilage covering the femur, the subchondral bone would be the femur and the vacuum delivery manifold 104 would be placed in the femur. Other suitable means in addition to drilling may be used for creating a space for the vacuum manifold 104.

The vacuum manifold 104 is connected to the reduced pressure source 120. The therapeutic solution 112 is delivered to the defect surfaces 49, 59 and the reduced pressure is applied to the vacuum manifold 104. In this embodiment, applying reduced pressure through the subchondral bone causes the therapeutic solution 112 to have a concentrated flow path represented by arrows 103 and 105 through the interior 122 of the defects 48, 58 toward the vacuum manifold 104. Reduced pressure applied through the vacuum manifold 104 induces fluid flow through the matrixes of the tibia 34, i.e., the subchondral bone, from the intra-articular space 62. The defects 48, 58 are typically the path of least resistance, and thus, the therapeutic solution 112 will have a concentrated flow path through the defects 48, 58 as indicated by the arrows 103 and 105.

In another illustrative embodiment, the system 100 may be operated by positioning the fluid delivery manifold 102 into the intra-articular space between two articulating surfaces such that the apertures 119 of the fluid delivery manifold 102 are positioned proximate a the cartilage being treated. The vacuum manifold 104 is positioned in the subchondral bone attached to the cartilage being treated. The therapeutic solution 112 is delivered into the intra-articular space and reduced pressure is applied to the vacuum manifold 104. Applying reduced pressure to the subchondral bone causes the therapeutic solution 112 to have a concentrated flow path through the interior of the cartilage being treated toward the vacuum manifold 104. Reduced pressure applied through the vacuum manifold 104 induces fluid flow through the matrixes of the subchondral bone, from the intra-articular space. Thus, the therapeutic solution is introduced into the interior of the cartilage instead of just the surface of the cartilage. Defects within the cartilage are typically the path of least resistance, and thus, the therapeutic solution 112 will have a concentrated flow path through the defects.

In yet another illustrative embodiment, the system 100 may be operated by positioning the fluid delivery manifold 102 on a first face of a cartilage defect and the vacuum manifold 104 on a second face of the cartilage defect. The first face of the cartilage defect generally opposes the second face of the cartilage defect In one embodiment, the fluid delivery manifold 102 is parallel to the vacuum manifold 104. In another embodiment, the fluid delivery manifold 102 is angled relative to the vacuum manifold 104. Therapeutic solution 112 is delivered to the fluid delivery manifold 102 and reduced pressure is applied to the vacuum manifold 104. Applying reduced pressure causes the therapeutic solution 112 to flow from the first face of the defect, through the defect, and out the second face of the defect to the vacuum manifold 104. Thus, the therapeutic solution 112 is applied to the interior of the cartilage defect and the surrounding cartilage.

The operation of the system, or steps of the methods, described herein may be carried out in any suitable order, or simultaneously where appropriate.

Another illustrative embodiment of a fluid delivery manifold 216 and a vacuum manifold 218 for use in a system such as the system 100 of FIGS. 1 and 4 is presented in FIGS. 5A-5C and FIGS. 6A-6C, respectively. The fluid delivery manifold 216 and the vacuum manifold 218 are similar to the fluid delivery manifold 102 and the vacuum manifold 104 of FIG. 1 but have a different shape. Referring to FIGS. 5A-5C, the fluid delivery manifold 216 has a rectangular portion 268 and a tubular portion 270. The rectangular portion 268 has one or more apertures 242 positioned on the rectangular portion 268. The apertures 242 may be positioned on a defect facing side 272 of the rectangular portion 268 for delivering the therapeutic solution 112 to the defect surfaces 49, 59. In another embodiment, the apertures 242 may be placed on multiple faces of the rectangular portion 268 instead of just the defect facing side 272. The tubular portion 270 has a circular cross-section and is operable to connect the fluid delivery manifold 216 to the fluid supply 110. The fluid delivery manifold 216 has a distal end 252, a distal section 254, and a proximal end 256. The distal end 252 and the distal section 254 are associated with the rectangular portion 268 of the fluid delivery manifold 216. In one embodiment, the distal end 252 may have an aspect ratio of height to width between about 0.5 and about 1 to aid in positioning of the fluid delivery manifold 216 into the intra-articular space between two articulating surfaces. For example, the distal end 252 may have a height between about 1 mm and about 6 mm and a width between about 1 mm and about 12 mm. It should be appreciated that the length of the distal section 254 may depend on the type of tissue site being treated. The distal end 252 may be either open or closed. The apertures 242 are located on the distal section 254 of the fluid delivery manifold 216. The proximal end 256 is associated with the tubular portion 270 of the fluid delivery manifold 216 and is operable to connect the fluid delivery manifold 216 to the fluid supply 110. The fluid delivery manifold 216 may be manufactured as a single piece, or the fluid delivery manifold 216 may be multiple pieces fixed together.

Figure 6C:
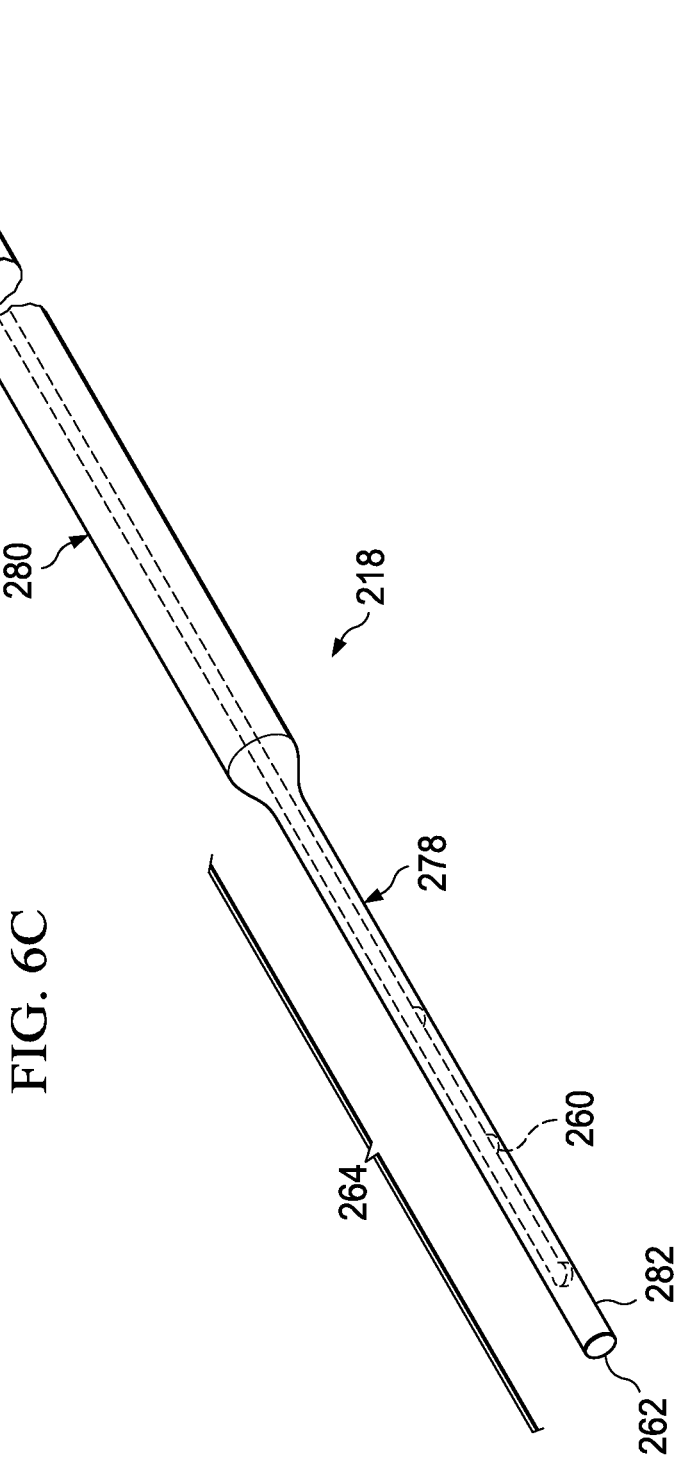
FIG. 6C is a schematic, perspective view of the fluid delivery manifold of FIG. 6A.

Similar to the fluid delivery manifold 216, the vacuum manifold 218, as shown in FIGS. 6A-6C, has a rectangular portion 278 and a tubular portion 280. The rectangular portion 278 has one or more apertures 260 positioned on the rectangular portion 278. The apertures 260 may be positioned on a defect facing side 282 of the rectangular portion 278 for delivering the reduced pressure to the defects 48, 58. In another embodiment, the apertures 260 may be placed on multiple faces of the rectangular portion 278 instead of just the defect facing side 282. The tubular portion 280 has a circular cross-section and is operable to connect the vacuum manifold 218 to the reduced pressure source 120. The vacuum manifold 218 has a distal end 262, a distal section 264, and a proximal end 266. The distal end 262 and the distal section 264 are associated with the rectangular portion 278 of the vacuum manifold 218. In one embodiment, the distal end 262 may have an aspect ratio of height to width between about 0.5 and about 1 to aid in positioning of the vacuum manifold 218 into the intra-articular space between two articulating surfaces. For example, the distal end 262 may have a height between about 1 mm and about 6 mm and a width between about 1 mm and about 12 mm. It should be appreciated that the length of the distal section 264 may depend on the type of tissue site being treated. The distal end 262 may be either open or closed. The apertures 260 are located on the distal section 264 of the vacuum manifold 218. The proximal end 266 is associated with the tubular portion 280 of the vacuum manifold 218 and is operable to connect the vacuum manifold 218 to the reduced pressure source 120. The vacuum manifold 218 may be manufactured as a single piece, or the vacuum manifold 218 may be multiple pieces fixed together.

Figure 7:
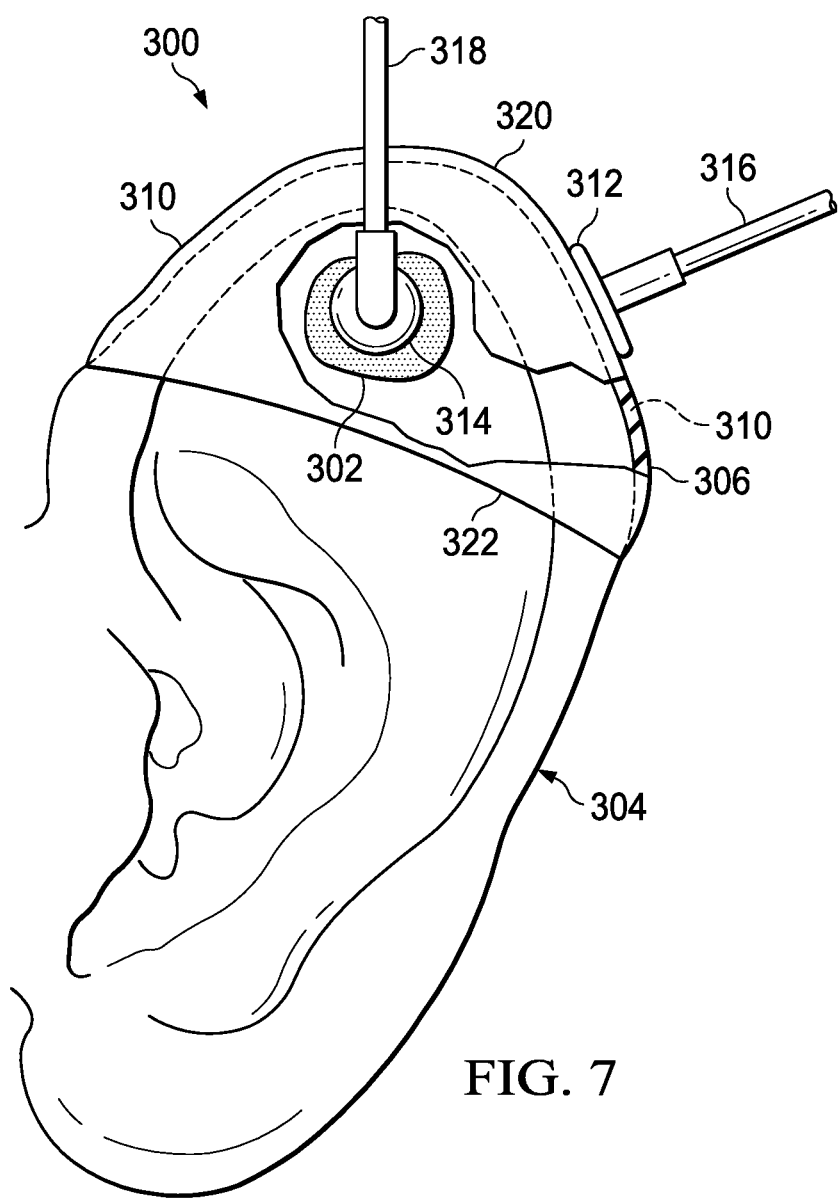
FIG. 7 is a schematic diagram, with a portion shown in cross-section, of an alternative embodiment for repairing cartilage in an ear using a reduced-pressure treatment system.

Referring now primarily to FIG. 7, an illustrative embodiment of a system 300 for stimulating cartilage formation at a tissue site 302 on top of an ear 304 is presented. This illustrative embodiment of the system 300 supplies a therapeutic solution, such as the therapeutic solution 112 of FIG. 1, and a reduced pressure to a cartilage defect 306, to regenerate the missing cartilage. The system 300 includes an ear mold 310, which may include a scaffold (not shown), configured for placement adjacent the cartilage defect 306 to provide a template for new cartilage formation. The system 300 further includes a reduced pressure interface 312 for providing fluid communication between a reduced pressure source and the tissue site 302, and a fluid delivery interface 314 for providing fluid communication between a therapeutic solution supply and the tissue site 302. A conduit 316 is connected to the reduced pressure interface and a conduit 318 is connected to the fluid delivery manifold 314. The reduced pressure interface 312 and the fluid delivery interface 314 are positioned on opposing faces of the ear mold 310. In one embodiment, the reduced pressure interface is connected to the medial face 320 of the ear mold 310 and the fluid delivery interface 314 is connected to the lateral face 322 of the ear mold 310.

The mold 310 may be placed adjacent to, in contact with, or substantially over the defect 306 to promote the growth of the cartilage in the defect 306. The mold 310 is a three-dimensional porous structure that provides a template for cell growth of the cartilage within the defect 306. Non-limiting examples of scaffold materials include calcium phosphate, collagen, PLA/PGA, hydroxyapatite, carbonates, and processed allograft materials. The mold 310 may also assist in delivering fluids to the tissue site 302. In some embodiments, the mold 310 is flexible to conform to the shape or contour of the defect 306 at the tissue site 302. The design of the mold 310 may also serve to prevent cartilage overgrowth. The shape and flexibility of the mold 310 may be selected without undue experimentation depending on the type of cartilage being treated in the location of the cartilage in the body treated.

The shape and flexibility of the mold 310 may be selected based on the desired shape of the ear 304. Once the mold 310 is created to fit the ear 304 at the tissue site 302 with the missing portion, it can be used to form a scaffold. The mold 310 may contain elements of the therapeutic solution 112 or the therapeutic solution 112 may be delivered to the scaffold 307 and thus the defect 306. U.S. Pat. No 8,197,806 to Girouard, entitled "Stimulation of Cartilage Formation using Reduced Pressure Treatment," describing a scaffold for use in generating cartilage in an ear defect is incorporated herein by reference.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. Moreover, the benefits and advantages described above may relate to one embodiment or may relate to several embodiments. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

What is claimed is:

1. A method for stimulating formation of cartilage at a defect in cartilage adjacent an articulating surface of a first bone or a second bone of at least two bones forming a joint the method comprising:
    positioning the distal end of a fluid delivery manifold having at least one aperture within the joint adjacent the articulating surface of the first bone;
    connecting the proximal end of the fluid delivery manifold to a fluid source containing a therapeutic solution;
    positioning the distal end of a vacuum manifold having at least one aperture within a condyle of either one of the first bone and the second bone;
    connecting the proximal end of the vacuum manifold to a reduced pressure source for delivering reduced pressure to the condyle;
    delivering the therapeutic solution to the defect; and
    delivering the reduced pressure to the condyle to draw the therapeutic solution from the fluid delivery manifold through the defect.

2. The method of claim 1, further comprising making an incision in soft tissue adjacent the joint and the first bone for positioning the fluid delivery manifold within the joint adjacent the defect and the articulating surface of the first bone.

3. The method of claim 1, further comprising drilling a hole into the condyle adjacent the opposing surface of the first bone for positioning the vacuum manifold within the condyle.

4. The method of claim 3, wherein the second bone is a femur.

5. The method of claim 3, wherein the second bone is a tibia.

6. The method of claim 1, further comprising delivering the therapeutic solution toward the defect in the first bone.

7. The method of claim 1, further comprising delivering the reduced pressure toward the defect in the first bone.

\* \* \* \* \*